United States Patent
Farone et al.

(10) Patent No.: US 7,667,062 B2
(45) Date of Patent: Feb. 23, 2010

(54) FATTY ACID CONTAINING COMPOUNDS AND METHODS OF USING SAME

(75) Inventors: William A. Farone, Irvine, CA (US); Tracy Palmer, Fallbrook, CA (US)

(73) Assignee: Regenesis Bioremediation Products, San Clemente, CA (US)

( * ) Notice: Subject to any disclaimer, the term of this patent is extended or adjusted under 35 U.S.C. 154(b) by 299 days.

(21) Appl. No.: 11/411,702

(22) Filed: Apr. 26, 2006

(65) Prior Publication Data
US 2006/0243669 A1    Nov. 2, 2006

Related U.S. Application Data

(60) Provisional application No. 60/675,694, filed on Apr. 28, 2005.

(51) Int. Cl.
C07C 57/00 (2006.01)
(52) U.S. Cl. .................................................. 554/227
(58) Field of Classification Search .................. 554/227
See application file for complete search history.

(56) References Cited

U.S. PATENT DOCUMENTS

| | | | |
|---|---|---|---|
| 5,265,674 A | 11/1993 | Fredrickson et al. |
| 5,277,815 A | 1/1994 | Beeman |
| 5,602,296 A | 2/1997 | Hughes et al. |
| 6,242,663 B1 | 6/2001 | Ponder et al. |
| 6,265,205 B1 | 7/2001 | Hitchens et al. |
| 6,420,594 B1 | 7/2002 | Farone et al. |
| 6,620,611 B2 | 9/2003 | Hince |
| 6,783,678 B2 | 8/2004 | Sorenson |
| 7,008,964 B2 | 3/2006 | Clausen et al. |

OTHER PUBLICATIONS

Goodman, Alan. Groundwater Pump and Treat . . . URL: http://costperformance.org/profile.cfm?ID=370&CaseID=370.

Primary Examiner—Deborah D Carr
(74) Attorney, Agent, or Firm—C. H. O'Donohue

(57) ABSTRACT

A novel series of compositions with aqueous chemicals decontamination activity and their uses is described. The preparation of esters of fatty acids with polyols that contain lactic acid is also described. These novel compositions release hydroxy acid and fatty acids slowly into water providing activity over long periods of time with the compounds exhibiting biodegradable characteristics and aiding in the biodegradation of contaminants.

12 Claims, 5 Drawing Sheets

IR SPECTRUM OF MIXED ESTER PRODUCT

FIGURE 1. IR SPECTRUM OF MIXED ESTER PRODUCT

FIGURE 2. IR SPECTRUM OF MIXED ESTER PRODUCT

FIGURE 3. COMPARISON OF COMPLETED VS. UNCOMPLETED REACTION.

FIGURE 4. IR SPECTRUM OF AN ALMOST COMPLETED REACTION.

Figure 5. The Treatment of TCE over Time

FATTY ACID CONTAINING COMPOUNDS AND METHODS OF USING SAME

This application claims the benefit of U.S. Provisional Application No. 60/675,694, filed Apr. 28, 2005.

FIELD OF THE INVENTION

The present invention is directed towards a novel series of compositions with aqueous chemicals decontamination activity and their uses. In another aspect the present invention is directed to the preparation of esters of fatty acids with polyols that contain lactic acid. These novel compositions are characterized by releasing hydroxy acid and fatty acids slowly into the water thus providing activity over long periods of time while exhibiting biodegradable characteristics such that the compositions of this invention do not remain in the water. These compositions are also the basis of formulations which provide a time-release source of lactic acid and other materials which stimulate growth of microbes and facilitate bioremediation.

The invention also comprises the novel compounds and their preparation and methods of using them.

BACKGROUND OF THE INVENTION

The following description of the background of the invention is provided to aid in understanding the invention, but is not admitted to be, or to describe, prior art to the invention. All publications are incorporated by reference in their entirety.

Chlorinated hydrocarbons have been widely used for several decades. Improper handling and storage along with the widespread usage, has led to extensive soil and groundwater contamination. These materials are among the most prevalent groundwater contaminants in the United States today. Contamination of groundwater by chlorinated hydrocarbons is an environmental concern because these compounds have known toxic and carcinogenic effects. Chlorinated hydrocarbons (CHCs) pose both environmental and health risks. CHCs can be highly toxic, and some have been found to be potential mutagens and carcinogens. This group of chemicals, which include DDT and DDE, were banned starting in the 70's with more of the volatile members of the group such as TCE being banned recently. They have been found to be very resistant to decay and to biodegradation.

Pump and treat methodologies historically and presently have been used to remove contaminants from water and the subsurface. This technique uses a series of extraction wells drilled into a contaminated aquifer, and the contaminated water is drawn through the extraction well and treated to remove or to degrade the contaminants. The water is then returned to the aquifer via an injection well. This technology typically is very expensive and is used in conjunction with other methodology such as, air sparging and soil vapor extraction. A Federal Remediation Round Table report issued in 2004 indicated that it took 13 years to remove a total of 958 pounds of volatile organic compounds (VOCs) at a site in Gresham, Oreg. at a cost of $2,540 per pound of VOC. (URL: http://costperformance.org/profile.cfm? ID=370 & CaseID=370 Page last modified on: Thursday, Apr. 7, 2005)

Anaerobic bacteria have also been employed in attempts to biodegrade chlorinated hydrocarbons in situ. Some species perform this function through reductive dechlorination. This process requires a steady supply of an electron donor such as hydrogen. Several methods have been proposed to supply this hydrogen (U.S. Pat. No. 5,277,815 and U.S. Pat. No. 5,602,296). As the hydrogen is immediately released in the treatment area, there is a need to constantly inject large volumes of solutions into the systems. The use of polymers in the form of granules, briquettes, pellets, tablets, and capsules have been attempted to provide slow release of soluble and insoluble organic substrates as a means of enhancing anaerobic bioremediation (Hince U.S. Pat. No. 6,620,611 B2). Fuel cells including multi-metallic particles have been used in a similar fashion (Hitchens et al. U.S. Pat. No. 6,265,205 B2). Zero valent iron has also been proposed to treat groundwater and surface streams for decontamination (Quinn et. al, U.S. Pat. No. 7,008,964 and Ponder et al, U.S. Pat. No. 6,242,663).

Farone et al. (U.S. Pat. No. 6,420,594) disclosed the composition and use of a series of polylactate esters that when placed in water under selected conditions slowly hydrolyze to release lactic acid. As the lactic acid is assimilated, it is gradually converted to acetic acid releasing hydrogen which is utilized by microbes to assimilate various chemicals such as chlorinated solvents, pesticides, and explosives that are present.

There have been attempts to use vegetable oils for a similar purpose (U.S. Pat. No. 5,265,674). Vegetable oils are not as biochemically efficient at producing hydrogen and they have the effect of being slower to be utilized by methanogenic bacteria thus keeping the oxidation reduction potential (ORP) in the ground water above the point of producing significant amounts of methane. A disadvantage of vegetable oil is that it is mobile and will move in the ground water. It is difficult to use vegetable oil as an injectable barrier such as that which the polylactate esters provide. In addition the movement of the oil can also mobilize the pools of contaminants making it difficult to ascertain where the oil/contaminants are traveling in the aquifer. The most rapid rate of decomposition of most of these contaminants occurs under acetogenic conditions (ORP is −100 mv to −200 mv). Under methanogenic conditions most of the chemical energy goes into producing methane and is therefore wasted (ORP is below −200 mv). Maintaining the correct ORP in the acetogenic range allows the degradation of the contaminants to proceed at a more rapid rate. This ORP effect is due to the fatty acids released from the oil by hydrolysis or partial utilization of the oil and not from the oil itself.

All of the previously mentioned methods have been shown to have serious shortcomings. Addition of non native materials adds additional foreign material to an already contaminated site. With materials that release immediately there is a requirement for frequent addition of remediation matter. This frequent addition of the chosen material is needed to keep a sufficient concentration in the contaminated area over time. The constant injection of high volumes of solutions will increase the volume of the system or aquifer and thereby potentially cause further spread of the contamination. Special measures are required to deoxygenate the water and solutions which are injected, to ensure maintaining the anaerobic atmosphere which fosters the reduction. Thus a need exists for a safe, cost-effective method for removing these contaminating materials from ground water and soils.

SUMMARY OF THE INVENTION

The present invention relates to compositions characterized by their ability to release fatty acids and lactate slowly over time. The present invention also relates to formulations comprising the compounds, as well as methods for their use in aiding bioremediation of media contaminated by organic contaminants as for example, halogenated hydrocarbons.

DEFINITIONS

In accordance with the present invention and as used herein, the following terms are defined with the following meanings, unless explicitly stated otherwise.

The term "lower" referred to herein in connection with organic radicals or compounds, respectively, defines such as with up to and including 6, preferably up to and including 4, and advantageously one to three carbon atoms. Such groups may be straight chain, branched, or cyclic.

The term "carboxyl" refers to —C(O)OH.

The term "carboxy esters" refers to —C(O)OR where R is alkyl optionally substituted.

The term "alkyl" refers to saturated aliphatic groups including straight-chain, branched chain, and cyclic groups. Alkyl groups may be optionally substituted. Suitable alkyl groups include methyl, isopropyl, ethyl, and cyclopropyl. Additional suitable alkyl groups include —$CH_2$—, —$CH_2CH_2$—, and —$CH(CH_3)$—.

The term "optionally substituted" or "substituted" includes both alkyl and aryl groups substituted by one to two substituents, independently selected from lower alkyl, oxygen, sulfur, nitrogen, and halogens.

The term "enhancing" refers to increasing or improving a specific property.

The term "administered simultaneously" refers to the administration of one composition at or near the same time in which another composition is administered. Preferably administration is within 30 minutes of one another.

The term "therapeutically effective amount" refers to an amount that has any beneficial effect in remediating aquifer, soil, wastestream, river(s) and river water, well(s) and well water, and any body of water.

The term "biodegradable" has its normal and usual meaning and may also refer to compounds that are readily utilized or degraded by naturally occurring microorganisms.

The term "polyol" refers to an alcohol having more than one hydroxyl radicals including glycols, sugars (both oxidized and reduced), and other multifunctional alcohols and carbohydrates The term "polylactate release compound composition" refers to compositions that serve as substrates that release hydroxy acid slowly over time as disclosed in U.S. Pat. No. 6,420,594 (incorporated by reference in its entirety). The composition further may contain one or more compounds selected from the group consisting of nutrients, buffers and pH modifiers, ethylene, chelating agents, surfactants, vitamins, enzymes, compounds that inhibit competing microorganisms, and bacteria and other microbes.

The terms "system" and "medium" refer to not only to sites, systems and media in nature such as soils, aquifers, lakes, rivers, and the like, but also to man-made systems including reservoirs, holding tanks, bioreactors, wastestreams, industrial processes, wells, and the like.

The term "fatty acids" refer to any saturated or unsaturated C6 to C22 carboxylic acids and includes those that occur naturally as an ester in fats, waxes, and essential oils or as glycerides in fats or fatty oils. This term includes those aliphatic monocarboxylic acids that can be derived from fat or vegetable oils (for example, tall oil, soybean oil, coconut oil, palm oil, corn oil, palm kernel oil, animal tallow) by hydrolysis and includes palmitic, stearic, myristic, caproic, oleic acids.

The term "ORP" refers to the oxidation reduction potential.

The term "vacuum" has its normal and usual meaning and may also refer to a space in which the pressure is lower than atmospheric pressure and can be expressed either in units of absolute pressure units or relative to atmospheric pressure. Usually relative vacuum is expressed in of inches of Hg relative to atmospheric wherein about 29.92 inches (760 mm) represents "total" vacuum equivalent to 0.0 mm Hg absolute.

The term "micelle" refers to aggregates of a material beyond its solubility limits in water that form stable groupings that can contain and hold in suspension water insoluble materials.

The term "HRC" refers to the compound as claimed in U.S. Pat. No. 6,420,594, claim 1 and as described in example 13 of U.S. Pat. No. 6,420,594.

The term "PED" refers to a compound of Formula I where z=1 and an R is:

$$CH_3(CH_2)_r-\overset{OH}{\underset{|}{CH}}-\overset{O}{\underset{\|}{C}}+O-\overset{CH_3}{\underset{|}{CH}}-\overset{}{\underset{\underset{O}{\|}}{\underset{|}{C}}}\!\!-O-\overset{CH_3}{\underset{|}{CH}}\quad CH_3,$$

(structural formula as depicted)

The following well known chemicals are referred to in the specification and the claims. Other abbreviations used and names are provided.

GPL: Glycerol polylactate;
CHC: Chlorinated hydrocarbons
DDT: Chlorophenothane; 1,1,1-Trichloro-2,2-bis(p-chlorophenyl)ethane; Dichlorodiphenyltrichloroethane;
DDE: 1,1-Dichloro-2,2-di(p-chlorophenyl)ethylene; Dichlorodiphenyldichloroethylene;
TCE: Trichloroethylene; 1,1-Dichloro-2-chloroethylene
PCE: Tetrachloroethylene; Perchloroethylene
Hg: Mercury

DETAILED DESCRIPTION OF THE INVENTION

In view of the existing methods, a need remains for a method utilizing a composition to provide remediation of organic contaminants in water that is cost-effective, safe, efficient, and requires a minimum of active management to perform. Furthermore, the composition would simultaneously release both lactate and fatty acids over a time period, would remain where injected, would be totally consumed leaving no residue, and would last for a period of time while releasing the desired compounds. The present invention provides novel compounds, formulations, and methods that exhibit some or all of these desirable qualities.

In one aspect the following compounds are included in the invention but the compounds are not limited to these illustrative compounds. The compounds are shown without depiction of stereochemistry. For example $R^1$, $R^2$, and $R^3$ may contain asymmetric centers.

Formula I

In another aspect the composition of Formula I is as shown below:

Formula I wherein $R^1$, $R^2$, and $R^3$ are independently selected from the group consisting of k is an integer from 1 to 13; m is an integer from 1 to 13; p is an integer from 1 to 13; r is an integer from 0 to 3; s and s" are integers from 0 to 2; n is an integer from 4 to 18; y is an integer from 0 to 6; z is an integer from 1 to 4; and where at least one of $R^1$, $R^2$, and $R^3$ is selected from the group consisting of The lactate esters are formed by removing water from lactic acid which is usually conducted under acid catalyzed conditions to make a polylactate. The polylactate molecules are then esterified to a polyol (e.g., glycerol, xylitol, sorbitol) backbone to make a saturated ester. Typically structures are given below:

n = 1 glycerol trilactate
n = 3 xylitol pentalactate
n = 4 sorbitol hexalactate
(common names)

A mixed structure is formed if some of the polylactate is replaced with fatty acids. As given below the ratio of fatty acid to polylactate is one mole of fatty acid to two moles of polylactate.

$$\begin{array}{c}
CH_2-O-\overset{O}{\underset{\|}{C}}-R^1 \\
(H\overset{|}{C}-O-CO-R^2)_z \quad \text{where } R^1 \text{ and } R^2 \text{ are} \\
CH_2O-\overset{|}{\underset{\|}{C}}-R^3 \\
O
\end{array}$$

$$CH_3-\overset{OH}{\underset{|}{CH}}-\overset{O}{\underset{\|}{C}}-O-\overset{CH_3}{\underset{|}{CH}} \quad CH_3$$
$$\overset{|}{\underset{\|}{C}}-O-\overset{|}{\underset{|}{CH}} \quad CH_3; \text{ and } R^3 \text{ is}$$
$$\overset{|}{\underset{\|}{C}}-O-\overset{|}{\underset{|}{CH}}$$
$$CH_3(CH_2)_p(CH=CH)_s(CH_2)_m(CH=CH)_{s''}(CH_2)_kCH_2;$$

s and s" are 0; m is 2; and p and k are each 7 to 8.

The ratios of polylactate to fatty acids can be different than those given above depending on the extent the polylactate is polymerized and the ratio of fatty acid used.

The mixed ester composition required certain characteristics. If the composition was too 'oily' or liquid, it would be mobile in the aquifer and would not perform the function of a barrier. A material that was too solid could not be easily injected into the aquifer. In another aspect the composition had to hydrolyze such that it produced therapeutically effective decontaminating amounts of both lactic acid and fatty acid. It was found that materials below a viscosity of about 8,000 cP typically lacked sufficient viscosity to remain where injected in an aquifer. If the viscosity was above 200,000 Cp, there was difficulty in injecting the material into aquifers since the material had poor flow characteristics. In one aspect materials in the viscosity range of about 15,000 to 30,000 cP were both injectable and remained localized as water flowed past and removed the hydrolyzed components. In another aspect the materials are mixed with water and injected into the aquifers and are distributed throughout the aquifers.

In a further aspect the composition acted on the undissolved phase of certain contaminants. The fatty acid component performed a micellization function while the lactate proved more rapid release of hydrogen resulting from microbial activity. As the contaminant is degraded the fatty acid helped to maintain the ORP and then was degraded. This combination of fatty acid acting as a carbon source and action in combining with the contaminant is referred to as partition electron donor.

Mixed Ester Example

A mixed ester was prepared by polymerizing lactic acid in the presence of an acidic catalyst. Phosphoric acid was used as the acidic catalyst. Glycerol and tall oil were added and the mixture heated to about 135° C. under a vacuum of 35 mm Hg absolute pressure. In another aspect the vacuum for the reaction was 3 to 55 mm Hg absolute pressure. The IR measurements were performed and a base was added when the ratio of IR peaks of the mixture at 1740 cm$^{-1}$ and 1720 cm$^{-1}$ was at least 2:1. The final viscosity was about 9,000 cP. In an additional aspect the final viscosity was 5,000 to 50,000 cP.

The preparation of the mixed esters can be effected by utilization of a fatty acid as the catalyst for the last stages of the lactic acid polymerization. In one aspect using fatty acids as the catalyst eliminated the use of other acid catalysts. The mixture was kept acidic with the addition of fatty acid during the second portion of the reactions. In another aspect, other acidic catalysts, such as phosphoric acid, are used. In a further aspect phosphoric acid was used as the catalyst as phosphates are acceptable environmentally and have been found to be biologically useful additives. The phosphoric acid was utilized to catalyze both the first reaction to form the polylactate followed directly by the second reaction to form the mixed ester by adding the fatty acids and the polyol. In a further aspect the polyol is selected from the group consisting of erythritol, xylitol, sorbitol, and pentaerythritol. At the end of the reaction, the remaining acid is neutralized. In one aspect there was a surprising relationship between the viscosity of the fluid and the amount of neutralization as the mixture exhibited a pseudogelatinous nature.

Figure 1:
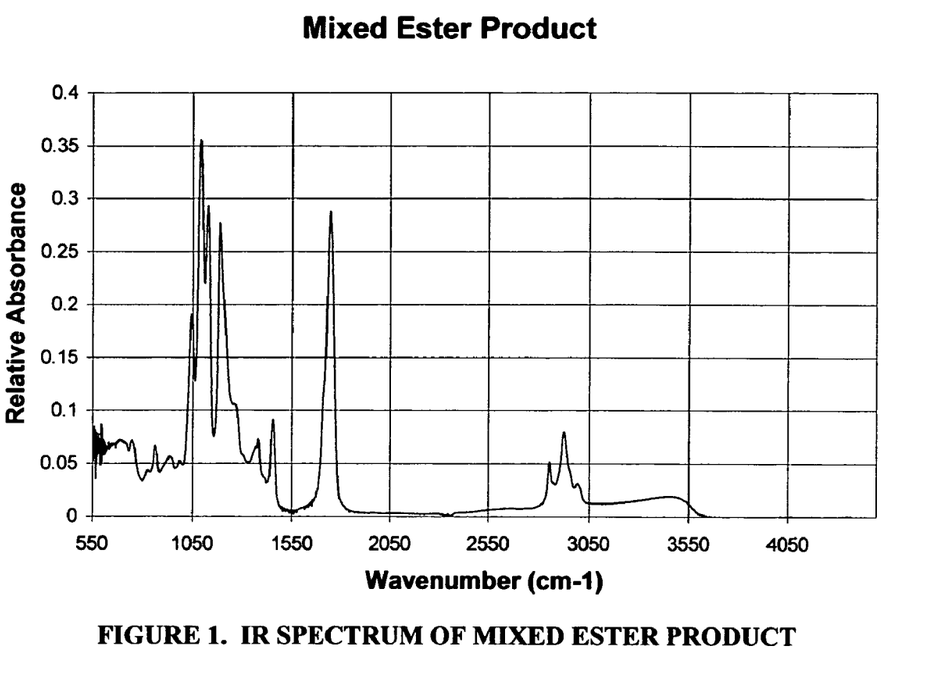
FIG. 1. IR spectrum of mixed ester product measured from 550 to 3550 $cm^{-1}$.
Figure 2:
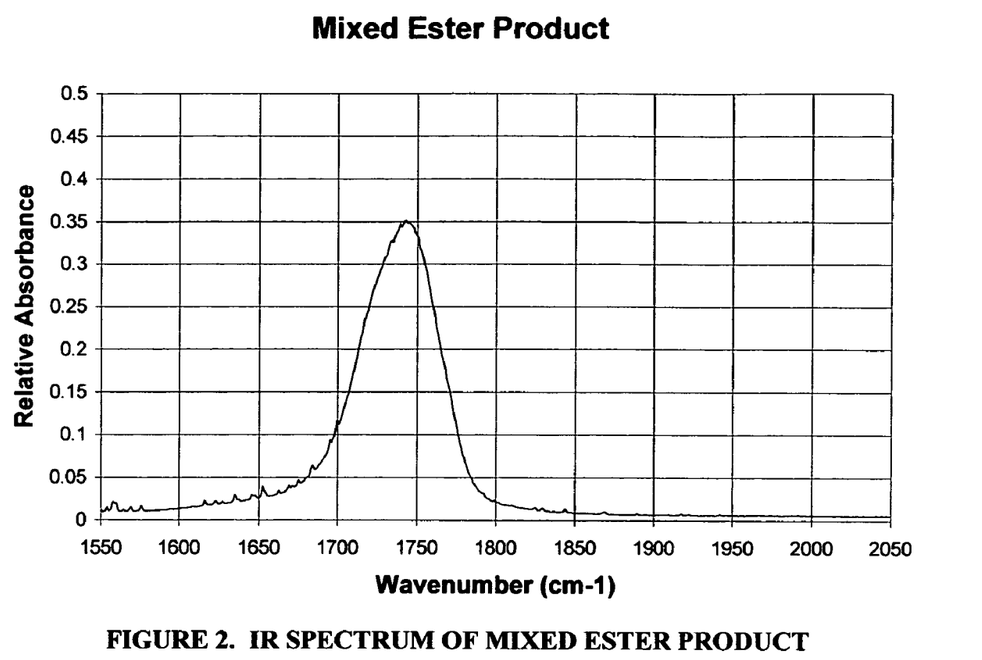
FIG. 2. IR spectrum of mixed ester product measured from 1550 to 2050 $cm^{-1}$.

Infrared spectrum was used to identify the reproducibility of the final product. FIG. 1 shows the IR spectrum of a typical mixed ester product. This spectrum is the mixed ester of the tetralactate and a mixture of tall oil fatty acids esterified to glycerol with two moles of fatty acid to one mole of tetralactate per mole of glycerol. In FIG. 2 the portion of the IR spectrum that is associated with organic acids (the carboxyl group) and esters is given. The ester content of the product is given by the peak that maximized at about 1740 cm$^{-1}$.

Figure 3:
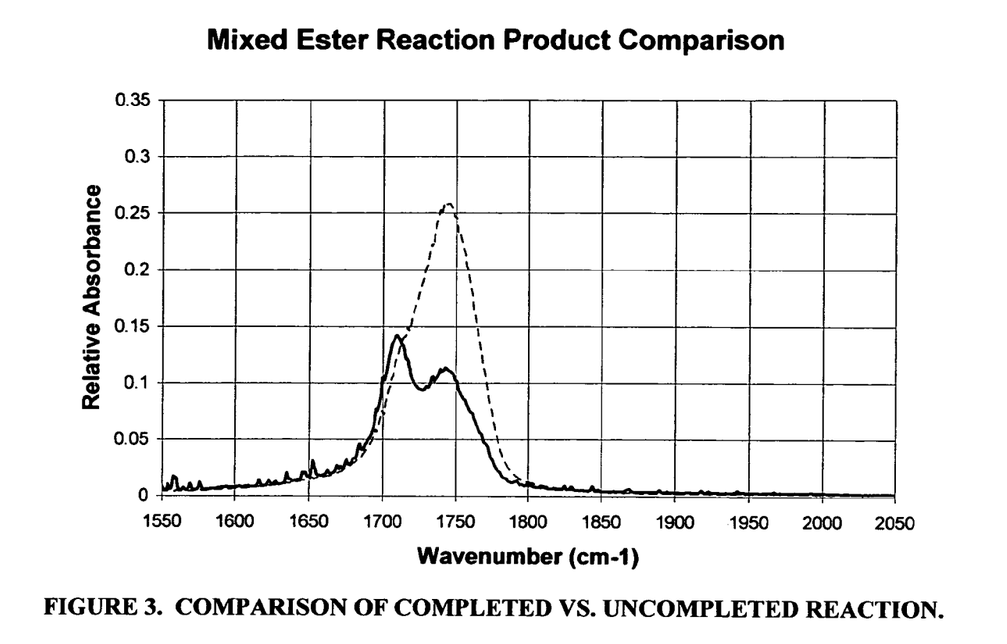
FIG. 3. IR spectra of mixed ester product from completed versus uncompleted reaction.
Figure 4:
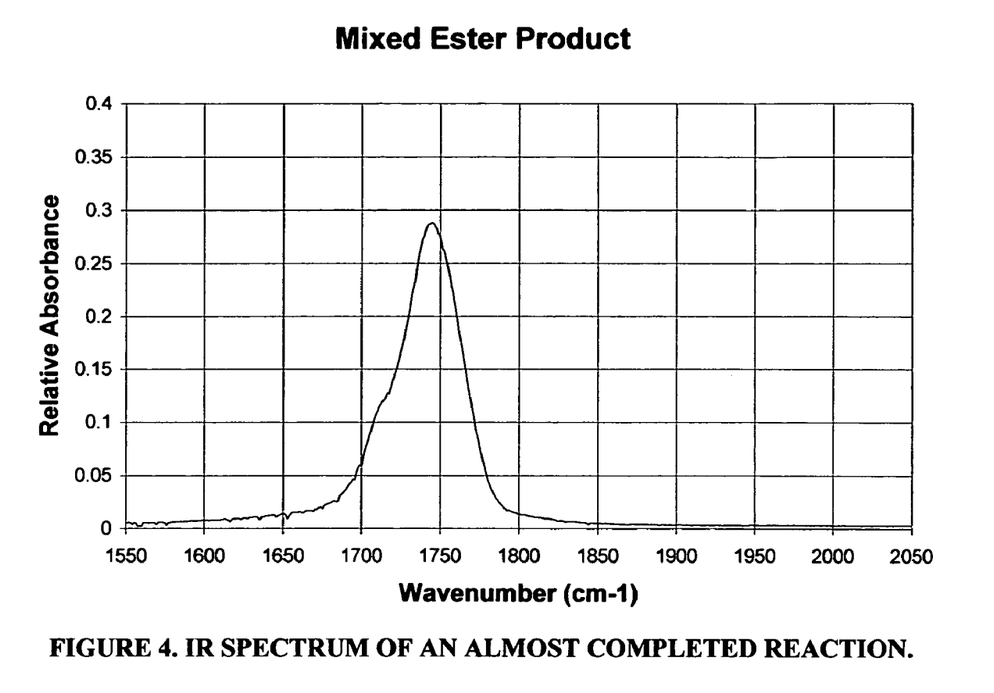
FIG. 4. IR spectrum of mixed ester product from reaction near completion.
Figure 5:
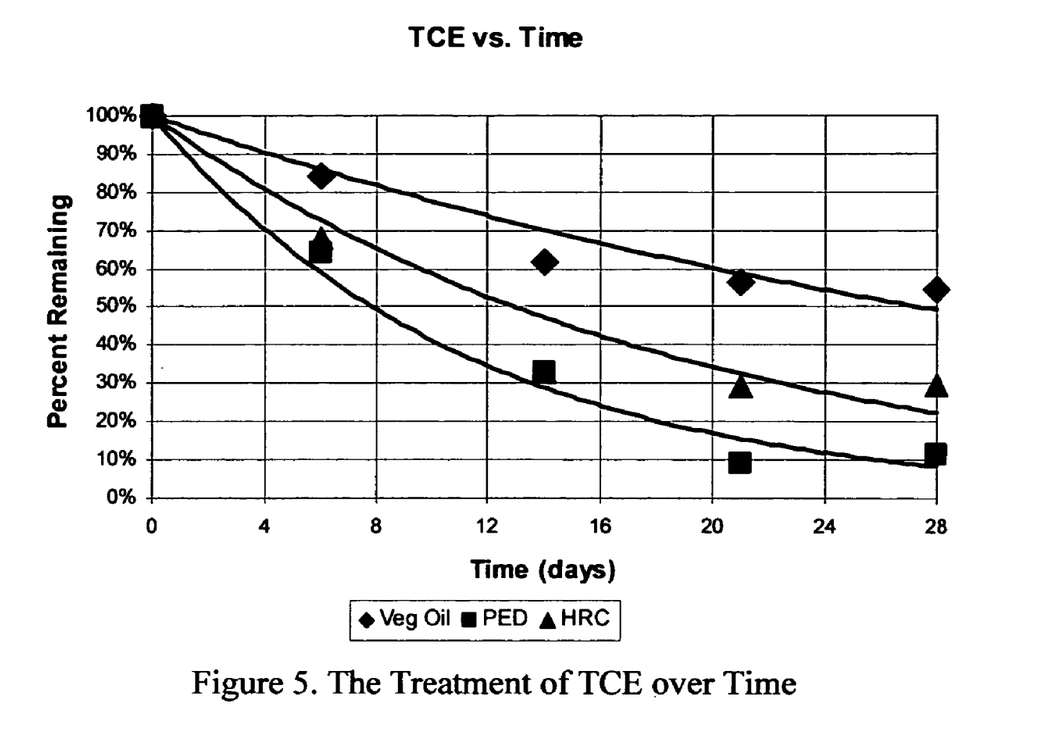
FIG. 5. Treatment of TCE over time.

In FIG. 3 a product from an incomplete reaction is compared to the product from a complete reaction. The peak at 1710 cm$^{-1}$ is the absorption of the carboxyl group of the unreacted acid. FIG. 4 shows similar product as shown in FIGS. 1 and 2 after several hours of reaction where the small amount of free acid is visible as the slight shoulder around 1715 cm$^{-1}$ on the main ester peak (1740 cm$^{-1}$).

Method for Determining Reaction End Point

The reaction mixture was determined to be complete when the ratio of the ester peak at 1740 cm$^{-1}$ to the fatty acid peak at 1720 cm$^{-1}$ was equal to or greater than 2 to 1. A single drop of the reaction fluid or a small portion of a solid was placed on a ZnSe crystal. The peaks were measured in a FTIR spectrophotometer, such as Shimadzu 8400S, with a 20,000 to 1 signal to noise ratio and 1 cm$^{-1}$ resolution. The spectrophotometer was equipped with a total internal reflectance attachment which contained the ZnSe crystal. Ratios higher than 2:1 were achieved when the esterification was complete. This FTIR method was also used to monitor the final product of the reaction.

Method for Bioremediation

The composition of Formula I

Formula I wherein $R^1$, $R^2$, and $R^3$ are independently selected from the group consisting of when at least one of $R^1$, $R^2$, and $R^3$ is selected from the group consisting of can be injected into the ground or groundwater for the treatment of aquifers, either alone or in combination with other treatments.

In another aspect a decontaminating amount of the composition is placed into a bed containing a substrate through which water flows and the contaminating chemicals are allowed to interact with the substrate.

In a further aspect the release of the organic acid from the hydrolysis of the decontaminating composition occurred over a time period of weeks to months.

Formulations

A composition containing 1-99% by weight a composition of Formula I

Formula I wherein $R^1$, $R^2$, and $R^3$ are independently selected from the group consisting of

$CH_3(CH_2)_p(CH=CH)_s(CH_2)_m(CH=CH)_{s''}(CH_2)_kCH_2$, and $CH_3(CH_2)_nCH_2$;

when at least one of $R^1$, $R^2$, and $R^3$ is selected from the group consisting of $CH_3(CH_2)_p(CH=CH)_s(CH_2)_m(CH=CH)_{s''}(CH_2)_kCH_2$ and $CH_3(CH_2)_nCH_2$, and when at least one of $R^1$, $R^2$, and $R^3$ is is combined with 0-50% polymer of lactic acid, 0-20% lactic acid and salts thereof; 1-99% fatty acid and salts thereof; and 0-5% salts containing potassium, sodium or phosphate. In one aspect this formulation is used for remediation. In another aspect the composition contains nutrients, buffers and pH modifiers, chelating agents, surfactants, vitamins, enzymes, bacteria, other microbes, and compounds that inhibit competing microorganisms.

Compounds/Compositions Prepared by the Invention 1.0

To a 1 L three-necked round bottom flask 300.00 gms. of lactic acid and 127.99 gms. of tall oil fatty acid were added. A mechanical stirrer was placed in one neck and the flask was heated to 135° C. under 28.8 inches of mercury. Excess tall oil fatty acid was used as the acid catalyst. After 6 hrs. 45.01 gms. of water was removed and collected in a receiver flask. Glycerin (38.25 gms.) was added to the reaction flask. The flask was heated to 135° C. under 28.5 inches of vacuum for three hours. IR spectrum showed that the product contained 2 mols of the polylactate tetramer and one mol of tall oil fatty acid. Viscosity measured 1000 cP.

2.0

To a 1 L three-necked round bottom flask 130.1 gms. of lactic acid and 233.35 gms. of tall oil fatty acid were added. The flask was heated with stirring to 135° C. under 29.8 inches of mercury. After 6.5 hours the water was removed and 38.03 gms. of glycerin was added to the reaction mixture. The reaction was continued for four additional hours at 135° C. under vacuum. Viscosity measured 1500 cP.

3.0

To a 1 L three-necked round bottom flask 319.34 gms. of lactic acid was added with 13.0 gms. of tall oil fatty acid. The flask was heated to 135° C. with stirring under full vacuum. At the end of 6 hours sample from the flask was analyzed by FTIR to verify that a tetramer was now present. 36.33 gms. of glycerin and 110.21 gms. of tall oil fatty acid were added to the reaction flask. The reaction was continued at 135° C. under full vacuum for 3 hours. Viscosity measured 2600 cP.

4.0

To a 1 L three-necked round bottom flask 305.08 gms. of lactic acid and 14.10 gms. of 85% phosphoric acid were added. The flask was heated under stirring to 135° C. under 29.2 inches of mercury. After the reaction ran for 7.5 hours and the water removed, 537.6 gms. of tall oil fatty acid and 21.9 gms. of glycerin were added. The reaction ran for an additional four hours at 135° C. at 29.5 inches of mercury. The reaction mixture was cooled to 60° C. and 13.98 gms. of KOH (potassium hydroxide) were added to neutralize the phosphoric acid. An IR sample verified presence of ester.

pH=5.4

Viscosity=22,400 cP 5.0

To a 12 L three-necked round bottom flask 3660.0 gms. of lactic acid and 195 gms. of 75% phosphoric acid were added. The flask was heated to 135° C. with stirring under 27.8 inches of mercury. After 11 hours and removal of the water, 935.21 gms. of glycerin and 5688.00 gms. of tall oil fatty acid were added. The reaction ran for an additional three hours and then the reaction mixture at 135° C. was neutralized with 195 gms. of KOH.

Viscosity=11,200 cP 6.0

150.0 lbs. of lactic acid was pumped into a 50 gal. pilot plant reactor and 8.1 lbs. of phosphoric acid was added. The reaction ran for 6.25 hrs. at 135° C. and 29.2 inches (742 mm) of mercury. After 6.5 hrs. 195.0 lbs. of tall oil fatty acid and 32.0 lbs. of glycerin were added to the reactor. After an additional 6 hrs. at 135° C. and 28.9 inches (734 mm) of mercury, a sample was taken and analyzed by FTIR to measure completeness of the reaction. The residual phosphoric acid was neutralized by 6.75 lbs. of KOH. There as a total of 73 lbs. of water removed during the reaction and 313.0 lbs. of product was produced.

Viscosity=5500 cP 7.0

To a one L three-necked round bottom flask 200.0 gms. of lactic acid and 10.8 gms. of 75% phosphoric acid were added. The flask was heated to 129° C. under 29.9 inches of mercury. After 6 hours, 260.0 gms. of oleic acid and 43.0 gms. of glycerin were added. The reaction ran for an additional four hours at 135° C. and 29.8 inches of mercury. After cooling to 50° C., 9.0 gms. of KOH was added to neutralize the mixture.

Viscosity=7500 cP 8.0

150.0 lbs. of lactic acid was pumped into a 50 gal. pilot plant reactor and 9.0 lbs. of 75% phosphoric acid was added. The reaction ran for 6.25 hrs with stirring at 132° C. and 28.7 inches (728 mm) of mercury. After 6.5 hrs. 195.0 lbs. of oleic acid and 32.3 lbs. of glycerin were added to the reactor. After an additional 6 hrs. at 135° C. and 29.1 inches (740 mm) of mercury, the residual phosphoric acid was neutralized by 7.0 lbs. of KOH. There was a total of 72 lbs. of water removed during the reaction and 328.0 lbs. of product was produced.

Viscosity=6200 cP 9.0

3300 lbs. of lactic acid was pumped into a 900 gal. production reactor and 158 lbs. of 75% phosphoric acid was added. The reaction ran for 8 hrs with stirring at 128.6° C. and 28.9 inches (734 mm) of mercury. After the 8 hrs 4275 lbs. of oleic acid and 703 lbs. of glycerin were added to the reactor. After an additional 4 hrs at 132° C. and 28.98 inches (736 mm) of mercury, the reactor was cooled to 117° C. and the residual phosphoric acid was neutralized by 148 lbs. of KOH. During neutralization the temperature increased to 132° C. There as a total of 1435 lbs. of water removed during the reaction and 7080 lbs. of product was produced.

Viscosity=91000 cP

Bioremediation Study

The bioremediation rates of three materials to treat TCE was studied. The three materials were vegetable oil, HRC (hydrogen release compound) and compound PED. Forty five test tubes were each filled with 10 grams of soil and 150 ml. of distilled water containing 15 to 22 ppm of TCE.

1. 3 grams of vegetable oil were added to fifteen test tubes containing 10 grams of soil, and 150 ml of distilled water containing 15 to 25 ppm of TCE.
2. 3 grams of HRC were added to fifteen test tubes containing 10 grams of soil, and 150 ml of distilled water containing 15 to 25 ppm of TCE.
3. 3 grams of compound A were added to fifteen test tubes containing 10 grams of soil, and 150 ml of distilled water containing 15 to 25 ppm of TCE.

The test tubes were sampled and analyzed once a week. Three test tubes from each group (1, 2, and 3) were analyzed at each sampling interval for statistical comparisons. At each sampling interval a new set of three test tubes were opened to eliminate any losses due to reopening test tubes each time to sample.

Typically these analyses are done every seven to ten days and the test is normally run for 4 to 6 weeks. The initial concentration of TCE was targeted at 20 ppm in all the sets of test tubes. Set 1 of the test tubes contained the vegetable oil. The initial concentration of TCE in this set of test tubes was on average 22.21 ppm. After 28 days there was a reduction of TCE in the vegetable oil set from the initial average concentration of 22.21 ppm to 12.12 ppm. Set 2 of test tubes contained HRC. There was a reduction of TCE from 14.20 ppm to 4.59 ppm after 28 days. Set 3 of test tubes contained Compound A. There was a reduction from the initial average concentration of TCE from 15.59 to 1.62 ppm of TCE in 28 days. The daughter products c-DCE, t-DCE and 1,1-DCE and VC were found to be present during the remediation. See Tables 1-9. ND in the tables refers to not detected and NC refers to no change.

TABLE 1

TCE Data
Average Concentration of TCE in ppm

| | Time | | | | |
|---|---|---|---|---|---|
| | 0 | 7 | 14 | 21 | 28 |
| Vegetable Oil | 22.21 | 20.65 | 13.67 | 12.50 | 12.12 |
| HRC | 14.20 | 10.01 | 5.15 | 4.54 | 4.59 |
| PED | 15.59 | 9.09 | 4.65 | 1.31 | 1.62 |

TABLE 2

TCE Data
Percent TCE Remaining

| | Time | | | | |
|---|---|---|---|---|---|
| | 0 | 7 | 14 | 21 | 28 |
| Vegetable Oil | 100.0% | 93.0% | 61.5% | 56.3% | 54.5% |
| HRC | 100.0% | 70.5% | 36.3% | 31.9% | 32.3% |
| PED | 100.0% | 58.3% | 29.8% | 8.4% | 10.4% |

TABLE 3 c-DCE Data
Average Concentration of c-DCE in ppm

| | Time | | | | |
|---|---|---|---|---|---|
| | 0 | 7 | 14 | 21 | 28 |
| Vegetable Oil | 0 | ND | ND | 4.45 | 2.03 |
| HRC | 0 | 0.51 | 0.12 | 1.17 | 0.13 |
| PED | 0 | ND | 0.5 | 1.31 | 0.31 |

TABLE 4 t-DCE Data
Average Concentration of t-DCE in ppm

| | Time | | | | |
|---|---|---|---|---|---|
| | 0 | 7 | 14 | 21 | 28 |
| Vegetable Oil | 0 | ND | ND | 0.62 | 0.70 |
| HRC | 0 | 0.21 | ND | 0.06 | ND |
| PED | 0 | ND | ND | 0.049 | 0.18 |

TABLE 5

1,1-DCE Data
Average Concentration of 1,1-DCE in ppm

| | Time | | | | |
|---|---|---|---|---|---|
| | 0 | 7 | 14 | 21 | 28 |
| Vegetable Oil | 0 | 2.22 | ND | 0.45 | 1.65 |
| HRC | 0 | 0.91 | 0.69 | 0.06 | 0.45 |
| PED | 0 | 0.83 | ND | 0.07 | 0.63 |

TABLE 6

VC Data
Average Concentration of VC in ppm

| | Time | | | |
|---|---|---|---|---|
| | 0 | 7 | 14 | 21 | 28 |
| Vegetable Oil | 0 | 3.74 | 0.72 | 0.56 | 1.26 |
| HRC | 0 | 0.31 | 0.34 | 0.23 | 0.16 |
| PED | 0 | ND | 0.28 | 0.07 | 0.09 |

TABLE 7

Lactic Acid Data
Average Concentration of Lactic Acid in ppm

| | Time | | | |
|---|---|---|---|---|
| | 0 | 7 | 14 | 21 | 28 |
| HRC | 0 | 3829 | 5473 | 7323 | 9721 |
| PED | 0 | 1310 | 891 | 570 | 1291 |

TABLE 8

Acetic Acid Data
Average Concentration of Acetic Acid in ppm

| | Time | | | |
|---|---|---|---|---|
| | 0 | 7 | 14 | 21 | 28 |
| HRC | 0 | 4390 | 5274 | 7961 | 3482 |
| PED | 0 | ND | 1052 | 385 | 408 |

TABLE 9

Pyruvic Acid Data
Average Concentration of Pyruvic Acid in ppm

| | Time | | | |
|---|---|---|---|---|
| | 0 | 7 | 14 | 21 | 28 |
| HRC | 0 | 358 | 14.55 | 10.77 | 18.72 |
| PED | 0 | ND | 16.04 | 2.23 | 8.01 |

TCE and its daughter products were measured by gas chromatography using a silica column on a SRI GC outfitted with both a PID (Photoionization Detector) and a FID (Flame Ionization Detector) detector. Toluene was used as the internal standard in a gas phase (head space) measurement. The hydrocarbons, methane, ethene and ethane are also detected on this column but the column conditions were not set to allow separation and quantification of the mixed hydrocarbons as methane from the HRC degradation on the column was also present.

The organic acids, lactic, pyruvic, acetic, propionic and butyric were measured using liquid chromatography with a Restek C18 column and an UV detector. Citric acid was used as the internal standard. For this procedure the column was quantitatively calibrated for lactic acid, pyruvic acid and acetic acid only. Lower concentrations of the organic acids were found in the compound A test tubes. This was due to the fact that there is not as much lactic acid present in the initial product. The compound A product was formulated with approximately ¼ the amount of lactic acid as compared the HRC product.

We claim:

1. A composition of Formula I;

Formula I wherein $R^1$, $R^2$, and $R^3$ are independently selected from the group consisting of k is an integer from 1 to 13;
m is an integer from 1 to 13;
p is an integer from 1 to 13;
r is an integer from 0 to 3;
s and s" are integers from 0 to 2;
n is an integer from 4 to 18;
y is an integer from 0 to 6;
z is an integer from 1 to 4; and
with the provisos that:
a) at least one of $R^1$, $R^2$, and $R^3$ is selected from the group consisting of b) at least one of $R^1$, $R^2$, and $R^3$ is 2. The composition of claim 1 wherein z is 1;

$R^1$ and $R^2$ are $R^3$ is s and s" are 0;
m is 2; and
p and k are each 7 to 8.

3. The composition of claim 2 wherein s is 1;
s" is 0;
m is 0;
p is 8; and
k is 8.

4. A process of making a composition of claim 1 comprising the steps of:
polymerizing lactic acid in the presence of a catalyst;
adding a polyol and a fatty acid;
heating mixture under vacuum; and
adding a base when ratio of IR peaks of mixture at 1740 $cm^{-1}$ and 1720 $cm^{-1}$ is 2:1 or greater.

5. The process of claim 4 wherein said polyol is selected from the group consisting of glycerol, erythritol, xylitol, sorbitol, and pentaerythritol.

6. The process of claim 4 wherein said catalyst is an acid.

7. The process of claim 6 wherein said acid is phosphoric acid.

8. The process of claim 4 wherein said fatty acid is tall oil fatty acid.

9. The process of claim 4 wherein said fatty acid is oleic acid.

10. The process of claim 4 wherein the temperature of reaction is between 120° C. and 145° C.

11. The process of claim 4 wherein said vacuum is from 3 to 55 mm Hg absolute pressure.

12. The process of claim 4 wherein the final viscosity is 5,000 to 50,000 cP.

* * * * *